United States Patent [19]

Kesling, Jr. et al.

[11] 4,236,023
[45] * Nov. 25, 1980

[54] PREPARATION OF UNSATURATED MONOESTERS BY THE CATALYTIC OXIDATIVE CARBONYLATION OF DIOLEFINS WITH AN ENOL ETHER OR 1-ALKOXYCYCLOALKENE

[75] Inventors: Haven S. Kesling, Jr., Drexel Hill, Pa.; Lee R. Zehner, Dublin, Ohio

[73] Assignee: Atlantic Richfield Company, Los Angeles, Calif.

[*] Notice: The portion of the term of this patent subsequent to Sep. 4, 1996, has been disclaimed.

[21] Appl. No.: 52,272

[22] Filed: Jun. 26, 1979

Related U.S. Application Data

[63] Continuation-in-part of Ser. No. 911,844, Jun. 2, 1978, abandoned.

[51] Int. Cl.³ ............................................... C07C 67/36
[52] U.S. Cl. .................................................... 560/207
[58] Field of Search ......................................... 560/207

[56] References Cited

U.S. PATENT DOCUMENTS

| | | | |
|---|---|---|---|
| 3,397,226 | 8/1968 | Fenton ................................. | 560/207 |
| 3,907,882 | 9/1975 | Gaenzler et al. ................. | 260/533 A |
| 4,065,490 | 12/1977 | Zehner ................................. | 560/204 |

FOREIGN PATENT DOCUMENTS 130714  10/1974  Japan.

OTHER PUBLICATIONS

Houben–Weyl, "Methoden der organischen Chemie", Georg Thieme Verlag., Band VII, Teil 1 at p. 436.
Tsuji, Jiro et al., "Organic Synthesis by Means of Noble Metal Compounds XIII, Carbonylation of Butadiene- and Isoprene–Palladium Chloride Complexes", J. Am. Chem. Soc., 87 (1965), pp. 4075–4079.

*Primary Examiner*—Natalie Trousof
*Assistant Examiner*—L. Hendriksen
*Attorney, Agent, or Firm*—Delbert E. McCaslin

[57] ABSTRACT

A process for the preparation of an unsaturated monoester having the formula

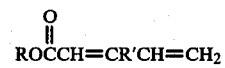

wherein R is an alkyl group of from 1 to 4 carbon atoms and R' is hydrogen, a halogen or a methyl group, by reacting carbon monoxide, oxygen, and at least a stoichiometric amount of an enol ether, or a 1-alkoxycycloalkene dehydrating agent with a diolefin having the formula

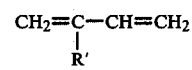

wherein R' is as hereinabove described, in the presence of a catalytic amount of a platinum group metal compound and a copper or iron oxidant salt compound.
Alternatively, a ligand or coordination complex compound of the metal salt compound and catalytic quantities of an alcohol may be employed.

24 Claims, No Drawings

PREPARATION OF UNSATURATED MONOESTERS BY THE CATALYTIC OXIDATIVE CARBONYLATION OF DIOLEFINS WITH AN ENOL ETHER OR 1-ALKOXYCYCLOALKENE

CROSS REFERENCE TO RELATED APPLICATIONS

This application is a continuation-in-part application of co-pending application Ser. No. 911,844, filed June 2, 1978, now abandoned, entitled PREPARATION OF UNSATURATED MONOESTERS BY THE OXIDATIVE CARBONYLATION OF DIOLEFINS WITH AN ENOL ETHER OR ALKOXYCYCLOALKENE.

BACKGROUND OF THE INVENTION

The oxidative carbonylation of mono-olefins such as ethylene and propylene to prepare carboxylic acids and derivatives employing various catalyst systems, particularly noble metal catalysts is known; see for example, Fenton and Steinwand, Journal of Organic Chemistry, Vol. 37, 2034 (1972) as well as U.S. Pat. Nos. 3,397,226; 3,876,694; 3,907,882; 3,923,883; and 3,960,934.

In an article by Jiro Tsuji, Accounts of Chemical Research, Vol. 2, 144, (1969) and especially bibliographic references (36) and (37) noted therein, the carbonylation of preformed butadiene-isoprene-palladium chloride complexes in alcohol to give 1,4-dichloro-2-butene and ethyl 3-pentenoate and ethyl 5-ethoxy-3-methyl-3-pentenoate and dimethyl butyrolactone, with other minor products is described. In a related article by S. Hosaka and J. Tsuji, Tetrahedron, Vol. 27, 3821–3829 (1971) the palladium catalyzed carbonylation in alcohol of various conjugated dienes and the reaction mechanism are shown.

A recent Japanese Kokai No. 75,130714, Oct. 16, 1975, describes the preparation of carboxylic acid esters by reacting conjugated dienes, carbon monoxide and at least stoichiometric amounts and generally an excess of a monohydric alcohol in the presence of molecular oxygen and a Group 8 noble metal catalyst. Dehydrating agents may be used if necessary to maintain non-aqueous conditions.

While oxidative carbonylation reactions are generally known, the prior art does not show or describe the process of the present invention for the oxidative carbonylation of a diolefin, such as butadiene, to selectively prepare diene monoester employing a stoichiometric or greater, i.e., an excess amount of an enol ether or a 1-alkoxycycloalkene as reactant, which monoester, may be further processed by catalytic dimerization, catalytic hydrogenation and catalyzed hydrolysis reaction sequences to prepare pelargonic and sebacic acid and related derivatives. Catalytic dimerization of the monoester, methyl penta-2,4-dienoate, can provide fatty acid precursors. The diene monoesters of the instant invention are especially useful as difunctional monomers for the preparation of speciality block, graft, and other polymers.

The process of the present invention is directed to the preparation of a diene monoester by the catalytic oxidative carbonylation of a diolefin. More particularly, the instant process relates to the synthesis of monoesters by reacting carbon monoxide, oxygen, a diolefin such as 1,3-butadiene, isoprene, chloroprene and the like, and at least a stoichiometric amount of an enol ether such as 2-methoxypropene or a 1-alkoxycycloalkene such as 1-methoxycyclohexene, under elevated temperature and pressure conditions in the presence of a catalytic amount of a ruthenium, rhodium, palladium, osmium, iridium or platinum metal salt compound or mixtures thereof, and a copper (I), copper (II), iron (II) or iron (III) oxidant salt compound. Co-catalytic ligands or coordination complex compounds of the metal salt compounds and catalytic quantities of a primary, secondary or tertiary saturated alcohol, while not required in the process of the invention, may also be employed.

The process of this invention provides an economic process for the selective preparation of a diene monoester, which may be a monobasic fatty acid or sebacic acid precursor, by the oxidative carbonylation of a conjugated diolefin such as butadiene. There is provided a good conversion of the diolefin employed especially 1,3-butadiene, and excellent yield selectivity to the diene monoester. Carbonate esters, oxalate esters, carbon dioxide as well as other side reaction products associated with the oxidative carbonylation reaction are obtained in only trace amounts or eliminated by the reaction conditions employed in carrying out the process of the invention. The reaction is catalytic in both the platinum metal salt compound and oxidant salt compound and employs at least stoichiometric quantities of reactant diolefins, carbon monoxide, oxygen and/or air, and enol ether or a 1-alkoxycycloalkene. The reaction can be safely and conveniently carried out under a non-explosive oxygen or air/carbon monoxide atmosphere.

SUMMARY OF THE INVENTION

According to the present invention diolefins are oxidatively carbonylated with carbon monoxide and oxygen or an oxygen-containing gas in the presence of a platinum group metal compound such as a palladium halide, a copper or iron oxidant salt compound such as a copper (I) iodide and a stoichiometric or greater amount of an enol ether or 1-alkoxycycloalkene such as 2-methoxypropene or 1-methoxycyclohexene respectively, to produce a diene monoester. The process is carried out at suitable temperatures and pressures and alternatively contemplates the use of catalytic quantities of an aliphatic alcohol and the use of catalytic amounts of various ligands, which will not work in themselves, in conjunction with the platinum group metal salt compound and the oxidant salt.

It is a primary object of this invention to provide a process for the preparation of diene monoesters in high yield and good conversion of reactants which monoesters may be further processed to pelargonic, other fatty acids, and sebacic acid derivatives.

It is another object of the invention to provide a novel reaction system for the conversion of carbon monoxide, oxygen, enol ethers and 1-alkoxycycloalkenes, and diolefins to diene monoesters.

It is a further object of this invention to provide a specific catalytic mechanism for the employment of platinum group metal compounds, oxidant salt compounds, and enol ethers or 1-alkoxycycloalkenes in an oxidative carbonylation process employing a diolefin.

These and other objects and advantages of this invention will become apparent from the description of the invention which follows and from the claims.

DESCRIPTION OF THE INVENTION

In accordance with this invention a diene monoester having the formula $$\underset{\text{ROCCH}=\text{CR'CH}=\text{CH}_2}{\overset{\text{O}}{\|}}$$

wherein R and R' are as hereinafter described, is produced by reacting, under liquid phase conditions, a mixture of carbon monoxide and oxygen or an oxygen-containing gas with a diolefin, and an enol ether or 1-alkoxycycloalkene, at elevated temperatures and pressures in the presence of a catalyst system comprising (1) a platinum group metal or platinum group metal compound or mixtures thereof, with or without a ligand or coordination complex compound such as lithium iodide, and (2) a catalytic amount of a copper (I), copper (II), iron (II) or iron (III) metal oxidant salt compound. The enol ether or 1-alkoxycycloalkene are employed in a stoichiometric or excess quantity, based on the diolefin being reacted, in order to essentially avoid the problems associated with the presence of water in the system which is produced therein by the oxidant-reoxidation reaction. While not essential to the oxidative carbonylation of the diolefin as set forth herein, a catalytic amount of an alcohol especially an aliphatic alcohol, is preferably employed in the reaction to aid in initiating the oxidative carbonylation reaction. 1-alkoxycycloalkenes are the preferred dehydrating agents. The reactants are initially charged in an essentially anhydrous condition.

A general postulated equation for the reaction of the present invention may for example be represented as follows:

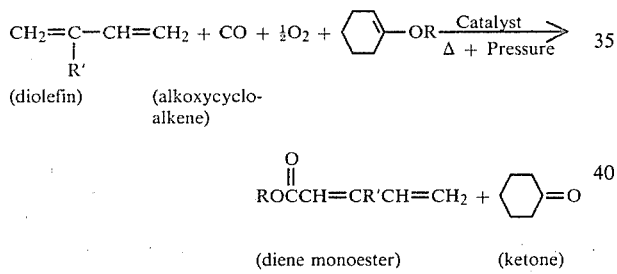

(diene monoester)    (ketone)

wherein R is an alkyl group of from 1 to 4 carbon atoms and R' is hydrogen, a halogen or a methyl group.

The reaction between the diolefin, carbon monoxide, oxygen and enol ether or 1-alkoxycycloalkene may be carried out in an autoclave or any other appropriate reactor. Although the order of addition of reactants and catalyst components may vary, a general procedure is to charge the diolefin, enol ether or 1-alkoxycycloalkene (preferably a 1-alkoxycycloalkene), platinum group metal compound and oxidant salt compound into the reaction vessel, and if desired a ligand or coordination complex compound and a catalytic quantity of an alcohol, then introduce the proper amount of carbon monoxide and oxygen to the desired reaction pressure and then heat the mixture to the desired temperature for the appropriate period. The reaction can be carried out batchwise or as a continuous process and the order of addition of reactants and catalyst may be varied to suit the particular apparatus employed. The addition of the oxygen or oxygen-containing gas, such as air, can be a pulsed or continuous addition to the reaction system. The reaction products are recovered and treated by any conventional method such as distillation and/or filtration, etc. to effect separation of the monoesters from unreacted materials, platinum group metal salt compound, oxidant salt compound, by-products, including for example, when reacting 1,3-butadiene, dimethyl hex-2,4-dienoate, methyl pent-3-enoate, dimethyl hex-3-endioate, methyl 3-methoxypent-4-enoate, methyl 5-methoxypent-3-enoate, dimethyl oxalate and $CO_2$, etc. Catalysts, including solvents which may have been employed, may be recycled to the system.

The diolefins which may be employed in concentrations of from about 10 to 80 weight percent, preferably 20 to 60 weight percent, or on a mole per mole basis with the enol ether or 1-alkoxycycloalkene employed, and suitable for use in the process of the present invention conform to the general formula $$CH_2=\underset{R'}{\underset{|}{C}}-CH=CH_2$$

wherein R' is hydrogen, a halogen or a methyl group. Representative diolefins within the above noted formula include for example, butadiene, isoprene, chloroprene, 2-bromobutadiene, 2-iodobutadiene, etc. Butadiene and isoprene are the preferred diolefins and butadiene is most preferred.

The enol ethers employed in at least stoichiometric quantities, and suitable for use in the process of the present invention conform to the general formula

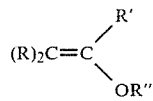

wherein R and R' may be hydrogen or an alkyl group containing from 1 to 4 carbon atoms. R" may be a substituted or unsubstituted alkyl group containing from 1 to 4 carbon atoms in the alkyl chain. Representative enol ethers suitable for use in this invention include for example, methyl vinyl ether, ethyl vinyl ether, n-propyl and isopropyl vinyl ether, n-butyl isobutyl and sec-butyl vinyl ether as well as t-butyl vinyl ether, etc., methyl-, ethyl-, propyl-, butyl-1-propenyl ether, etc.

The 1-alkoxycycloalkenes which may be employed in at least stoichiometric quantities, and suitable for use in the process of the present invention conform to the general formula

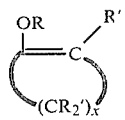

as indicated hereinabove, wherein R is an alkyl group containing 1 to 4 carbon atoms. R' may be hydrogen or a straight or branched chain alkyl group containing from 1 to 4 carbon atoms in the alkyl chain. X is an integer of from 3 to 6 thus forming a cyclic ring which may have from 5 to 8 carbon atoms.

Representative 1-alkoxycycloalkenes suitable for use in this invention include for example, 1-methoxy-, 1-ethoxy-, 1-propoxy-, 1-butoxy-, 1-isobutoxy-, etc. cyclohexenes, cycloheptenes, cyclopentenes, cyclooctenes, etc., 1-methoxy-4-methylcyclohexene, 1-methoxy-4-ethylcyclohexene, 1-methoxy-2-methyl-4- ethylcyclohexene, 1-ethoxy-4-butylcycloheptene, 1-methoxy-2-methyl-6-ethylcyclooctene, etc.

The alcohols which may be employed in catalytic quantities to aid initiating the oxidative carbonylation reaction and suitable for use in the process of the present invention can be monohydric saturated aliphatic alcohols and may contain other substituents such as amido, alkoxy, amino, carboxy, cyano, etc. radicals in addition to the hydroxyl group. The substituents, in general, do not interfere with the reaction of the invention.

The alcohols which may be employed in concentrations of from 0 to 20 and preferably 0.5 to 10 weight percent of the diolefin employed may be primary, secondary or tertiary alcohols and conform to the general formula ROH, wherein R is an optionally substituted aliphatic group preferably containing from 1 to 4 carbon atoms. Representative alcohols especially suitable for use in this invention are saturated monohydric alcohols such as methyl, ethyl, n-, iso, sec-, and tert-butyl, and n- and isopropyl alcohols. The preferred alcohols are the primary and secondary monohydric saturated aliphatic alcohols, such as methanol, ethanol, 1- and 2-propanol and n-butyl alcohol, etc. The R group of the alcohol if employed may be different from the R' or R" of the enol ether or 1-alkoxycycloalkene dehydrating agents noted hereinabove, resulting in the preparation of mixed diene monoesters.

The platinum group metal compounds which may be employed in the process of this invention as catalyst are the palladium, platinum, rhodium, ruthenium, iridium, and osmium salts or mixtures thereof. Among the chemical forms of the platinum group metal salt compounds which can be used as such or as mixtures or formed in the reaction system from the metals per se are for example the palladium, platinum, rhodium, ruthenium, iridium, and osmium, halides, sulfates, nitrates, oxides, oxalates, acetates and trifluoroacetates, preferably the palladium (II) halides, particularly palladium (II) iodide. Reresentative catalytic platinum group metal salt compounds include, for example palladium (II) iodide, $\pi$-allyl palladium iodide, platinum (II) iodide, rhodium (III) iodide, ruthenium (III) iodide, palladium (II) sulfate, palladium (II) acetate, palladium (II) trifluoroacetate, palladium (II) bromide, rhodium (III) bromide, iridium (III) chloride, platinum (II) sulfate, osmium (II) chloride, palladium (II) oxide, osmium tetroxide, iridium (III) sulfate, etc. As indicated above the metals as such may be added to the reaction as part of the catalyst mixture, the salt compound being formed in situ from at least a portion of the platinum group metal under reaction conditions.

The palladium, platinum, rhodium, ruthenium, osmium and iridium compounds employed may be in a homogeneous state in the reaction mixture at reaction conditions. Thus, the compounds may be present in solution, or suspension and may also be on support materials such as alumina, silica gel, aluminosilicates, activated carbon or zeolites or may be anchored to a polymer support. The compounds may be partially or completely soluble under reaction conditions. The reaction is generally carried out in the presence of a catalytic proportion of the platinum group metal salt compound and will proceed with small amounts of the metal salt compounds hereinabove described. Generally the proportions of the platinum group metal salt compound used in the reaction will be equivalent to between about 0.001 to 5 weight percent of the diolefin employed and are preferably employed in amounts between about 0.01 to 2 percent by weight of the diolefin employed. Larger or smaller amounts may be employed at varied pressures and temperatures.

As mentioned hereinabove, alternatively, a ligand or coordination complex compound of the platinum group metal salt compound may be employed in the process of the invention as co-catalyst in the catalytic mixture and thereby also achieve a pronounced increase in the selectivity for the diene monoester. The ligands may be, for example, alkyl or aryl phosphines, arsines, or stibines or salts of the alkali metals, e.g., lithium sodium, potassium, rubidium, cesium salts, such as lithium iodide, sodium iodide, potassium iodide, lithium acetate, lithium bromide, etc. The complexes of the metal salt compounds which are suitable for use in the process of the present invention include complex compounds of palladium, platinum, rhodium, ruthenium, osmium and iridium. The complex compounds may contain one or more atoms of the salt metals in the molecule and when more than one such atom is present, the metals may be the same or different. The mono- or polydentate ligands which are present in the molecule of the complex compounds and in which at least one of the electron-donating atoms is an atom of phosphorus, arsenic or antimony or a halide ion containing a lone pair of electrons may be, for example, organo-phosphines, -arsines and -stibines and their oxides. Suitable monodentate ligands include alkyl phosphines such as trimethylphosphine and tributylphosphine, arylphosphines such as diethylphenylphosphine and radicals derived from such phosphines, for example the radical having the formula —P(CH$_3$)$_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is preferred to employ the alkali metal halides, particularly the lithium halides such as lithium bromide and lithium iodide.

Benzonitrile, acetonitrile, isocyanates, isothiocyanates, pyridine, pyridyls, pyrimidine, quinoline. isoquinoline may also serve as suitable ligands to modify the platinum group metal catalyst activity or catalyst solubility.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and SnCl$_3$— groups; molecules which may be bonded to the metal include, for example organic isocyanides and isothiocyanates. Examples of suitable complex compounds are those represented by the following formulae:

| | |
|---|---|
| RhBr$_3$(PPhEt$_2$)$_3$ | Rh(CO)Cl(AsEt$_3$)$_2$ |
| Rh(CO)(PPhEt$_2$)$_2$ | RhCl(CO)(PEt$_3$)$_2$ |
| Rh(Ph$_2$PCH$_2$CH$_2$PPh$_2$)$_2$I | PdBr$_2$(PPh$_3$)$_2$ |
| Rh[(PhO)$_3$P]$_3$I | PdI$_2$(PPh$_3$)$_2$ |
| Li$_2$PdI$_4$ | PtCl$_2$(p-ClC$_6$H$_4$PBu$_2$)$_2$ |

-continued (PhCN)₂PdI₂

The complex compounds employed may be introduced into the reaction mixture as such, or they may be formed in situ from a suitable platinum group metal or metal compound noted above and the desired ligand.

The ligand or complex compounds are preferably employed and may be used in catalytic amounts of from 0 to 3 percent preferably from 0.1 to 1 percent by weight of the diolefin to be reacted although larger or smaller amounts may be employed at varied pressures or reaction rates.

The oxidant salt compounds which may be employed in an essentially anhydrous condition in the process of the present invention and in catalytic amounts of from 0.1 to 10 weight percent preferably 0.50 to 6 weight percent include the iron (II), iron (III), copper (I) and copper (II) salts such as the halides, sulfates, trifluoroacetates, nitrates, oxalates, naphthenates, hex-3-endioates or acetates and preferably copper (I) iodide and iron (II) iodide. Representative oxidant salts include, for example, copper (II) sulfate, copper (II) trifluoroacetate, copper (II) acetate, copper (II) oxalate, copper (II) triflate, copper (II) fluorosulfonate, copper (I) bromide, copper (I) sulfate, iron (III) sulfate, iron (II) bromide, iron (II) chloride, iron (III) acetate, iron (III) oxalate, copper (II) penta-2,4-dienoate, iron (II) penta-2,4-dienoate and iron (III) trifluoroacetate.

While not necessary to the reaction of the present invention, it is often desirable to add a small amount of an acid to aid in initiating the reoxidation (by oxygen) of copper (I) to copper (II) or iron (II) to iron (III). Suitable acids include for example hydroiodic, hydrobromic, sulfuric, phosphoric and acetic in concentrations of from 0-2 weight percent of diolefin.

Solvents, if desired, which are chemically inert to the components of the reaction system may be employed, and in some cases, especially in the oxidative carbonylation of 1,3-butadiene, will improve the selectivity and conversion to the desired diene monoester as well as the catalyst solubility or boiling point range for product and catalyst recovery. Suitable solvents include for example, dioxane, dimethylcarbonate, dimethyladipate, benezene, nitrobenzene, acetonitrile, tetrahydrofuran, methyl acetate, ethyl acetate, isopropyl acetate, n-propyl formate, butyl acetates, cyclohexyl acetate, n-propyl benzoate, lower alkyl phthalates, etc. the alkyl sulfones and sulfoxides such as propyl ethyl sulfoxide, diisopropyl sulfone, diisooctyl sulfoxide, acetone, cyclohexanone, methyl formate, etc.

The process of the present invention can be suitably performed by introducing the oxygen and carbon monoxide at a desired pressure into contact with the diolefin, alcohol, enol ether or 1-alkoxycycloalkene, the platinum group metal salt compound and the copper or iron oxidant salt and preferably a co-catalytic amount of a ligand or coordination complex and heating to the desired temperature. In general, a carbon monoxide pressure of about 15 psig to about 5000 psig partial pressure and preferably from 100 psig to about 2000 psig is employed. Stoichiometric quantities of carbon monoxide are generally employed. However, an excess of carbon monoxide may be employed, for example, in continuous processes where a large excess of or high carbon monoxide requirements are generally utilized, a suitable recycle of the unreacted carbon monoxide may be employed. The reaction will proceed at temperatures of from about 25° C. to 200° C. It is generally preferred to operate the process at temperatures in the range of 80° C. to 150° C. to obtain a convenient rate of reaction with the particular diolefin. Lower temperatures may be employed but the reaction rate is slower. Higher temperatures may also be used depending on the diolefin to be reacted. At the higher temperatures the diolefin employed may be in the vapor state. Heating and/or cooling means may be employed interior and/or exterior of the reaction to maintain the temperature within the desired range.

At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent. Oxygen itself may be diluted with an inert gas such as nitrogen, carbon dioxide or helium.

The reaction time is generally dependent upon the diolefin being reacted, temperature, pressure and on the amount and type of the catalyst, oxidant, alcohol and enol ether or 1-alkoxycycloalkene being charged as well as the type of equipment being employed. Reaction times will vary dependent on whether the process is continuous or batch and may vary from 10 to 600 minutes. Reaction time for butadiene is generally about 120 minutes.

The following examples are provided to illustrate the invention in accordance with the principles of this invention but are not to be construed as limiting the invention in any way except as indicated by the appended claims.

Although the process of the present invention will primarily be directed to the oxidative carbonylation of 1,3-butadiene to produce the diene monoester, methyl penta-2,4-dienoate, which is an important precursor for the preparation of pelargonic and sebacic acid, it is not intended that the process be limited to the butadiene type diolefins and those skilled in the art will recognize that the present invention is broadly applicable to the oxidative carbonylation of other conjugated diolefins, within the formula as hereinabove set forth, to produce other unsaturated monoester products.

In the examples which follow the reactions were carried out in a 500 ml. nickel-molybdenum (HASTELLOY alloy) stirred autoclave or 500 ml. titanium lined stirred autoclave. The liquid feed and solid catalyst components were charged into the autoclave as homogeneous solutions where possible. The diolefins were charged into a sight glass and allowed to come to thermal equilibrium before being charged into the autoclave as a liquid under pressure. Carbon monoxide was charged into the autoclave to the desired pressure followed by heating to the desired reaction temperature. Total system pressure was adjusted to the desired level by the addition of more carbon monoxide. Oxygen or air was added and a non-explosive carbon monoxide/oxygen gas mixture maintained. Where oxygen was employed, carbon monoxide was pulsed into the autoclave to sweep the oxygen out of the pressure tubing. Cooling water was circulated through the internal autoclave cooling coils to maintain the desired reaction temperature and to control the reaction exotherm observed upon the addition of reactant oxygen. After each gas uptake levelled out, total system pressure was readjusted and addition oxygen added. The procedure of charging oxygen or air increments and sweeping out the pressure lines with CO was repeated until no more gas uptake was observed or for the desired reaction time.

Upon completion of the reaction, the reactor was cooled to ambient temperature and vented to ambient pressure and gas samples obtained. Solids were separated from liquids by vacuum filtration. The gaseous product volume was measured and analyzed by mass spectral analysis (MS) and the liquid product was analyzed by gas-liquid chromatography (glc).

Diolefin conversions were calculated on the basis of moles of diolefin consumed by the reaction. Product selectivities were based on the millimoles of diolefin required to make the diene monoester and byproducts. The amount of unreacted diolefin was obtained by MS analysis of the gases and glc analysis for diolefin in the liquid product.

EXAMPLES 1 to 4

In Examples 1 to 4 a catalytic amount of no alcohol and a stoichiometric amount of 1-alkoxycycloalkene dehydrating agent was charged into the autoclave along with 1.51 g. (4.2 mmole) palladium (II) iodide, 1.98 g. (10.4 mmole) copper (I) iodide and 1.12 g. (8.4 mmole) lithium iodide. 1,3-butadiene was charged into the autoclave as a liquid under pressure. The reaction temperature was 100° C. and the total initial carbon monoxide pressure was 900 psig. The reaction was initiated by a 50 psig charge of oxygen and 50 psig line purging charge of carbon monoxide giving a total system pressure of 1000 psig. A strong exotherm and pressure drop of 75–100 psig over a course of 20 minutes was observed. The oxygen cycle was repeated five more times in increments of 25 psig oxygen and 50 psig carbon monoxide at intervals of 20 minutes during an autoclave residence time of 120 minutes. A total pressure drop of about 600 psig was observed. The reaction was terminated before completion and the autoclave cooled to ambient temperature and vented to ambient pressure. The alcohol, 1-alkoxycycloalkene and amount of 1,3-butadiene employed and analytical results giving the conversion and selectivities to product methyl, ethyl and butyl penta-2,4-dienoate shown in Table 1.

TABLE I

| Ex. | 1,3-butadiene Charged g. (mmoles) | Alcohol (mmole) | Dehydration[1] Agent (mmole) | 1,3-Butadiene Conversion (%) | Ester Selectivity Based on 1,3-Butadiene |
|---|---|---|---|---|---|
| 1 | 27 g. (500) | $CH_3OH$ (25) | MOC (500) | 21 | 83 mole % |
| 2 | 27 g. (500) | $C_2H_5OH$ (25) | EOC (500) | 18 | 80 mole % |
| 3 | 27 g. (500) | $C_4H_9OH$ (25) | BOC (500) | 17 | 79 mole % |
| 4 | 54 g. (1000) | — | MOC (1000) | 15 | 81 mole % |

[1]MOC - 1-methoxycyclohexene
EOC - 1-ethoxycyclohexene
BOC - 1-butoxycyclohexene

EXAMPLES 5 to 21

In Examples 5 to 21 which follow in table form the procedure and general operating conditions of Examples 1 to 4, except as specifically noted, was repeated employing 1 mole of diolefin, 1 mole of enol ether or 1-alkoxycycloalkene, 25 mmoles of an alcohol if employed, 5.0 millimole of platinum group metal compound catalyst, oxidant salt compound and with or without a ligand compound. Gaseous and liquid products were analyzed by mass spectral analysis (MS) and gas-liquid chromatography (glc) respectively.

The reaction conditions, reactants, catalysts and oxidants employed in Examples 5 to 21 are set forth in Table 2 with the results showing the main product yield, percent diolefin conversion and mole percent selectivities based on the diolefin summarized in Table 3.

TABLE 2

| Ex. | °C. Temp. | (psig) Pressure | Time Mins. | (1 mole) Diolefin | Alcohol (mmole) | Dehydration Agent | (5.0 mm) Catalyst | Oxidant (mmole) | Ligand (mmole) |
|---|---|---|---|---|---|---|---|---|---|
| 5 | 100 | 1000 | 120 | BD[1] | MeOH[2] (25) | MOC[3] | $PdI_2$ | CuI (12.5) | LiI (10.0) |
| 6 | 100 | 1000 | 120 | BD | MeOH (25) | MOP[4] | $PdI_2$ | CuI (12.5) | LiI (10.0) |
| 7 | 110 | 1200 | 125 | BD | MeOH (25) | MOC | $PdI_2$ | $FeI_2$ (25.0) | LiI (10.0) |
| 8 | 120 | 1000 | 130 | BD | MeOH (25) | MOC | $PdBr_2$ | $CuBr_2$ (12.5) | LiBr (10.0) |
| 9 | 100 | 1000 | 120 | BD | MeOH (25) | MOP | $PdBr_2$ | CuI (12.5) | LiBr (10.0) |
| 10 | 125 | 450 | 120 | IP[5] | MeOH (25) | MOC | $PdI_2$ | CuI (25.0) | LiI (10.0) |
| 11 | 100 | 1800 | 120 | IP | None | MOC | $PdI_2$ | $FeI_2$ (25.0) | LiI (10.0) |
| 12 | 125 | 3000 | 120 | IP | MeOH (25) | MOC | $PdBr_2$ | $FeI_2$ (25.0) | LiI (10.0) |
| 13 | 125 | 2000 | 120 | BD | MeOH (25) | MOC | $PtI_4$ | CuI (25.0) | LiI (10.0) |
| 14 | 125 | 2000 | 120 | BD | MeOH (25) | MOC | $RhI_3$ | $CuCl_2$ (25.0) | LiCl (10.0) |
| 15 | 100 | 1000 | 120 | BD | MeOH (25) | MOC | $Na_2PdI_4$ | CuI (25.0) | — |
| 16 | 100 | 1800 | 120 | BD | None | MOC | $K_2PdI_4$ | CuI (25.0) | — |

TABLE 2-continued

| Ex. | °C. Temp. | (psig) Pressure | Time Mins. | (1 mole) Diolefin | Alcohol (mmole) | Dehydration Agent | (5.0 mm) Catalyst | Oxidant (mmole) | Ligand (mmole) |
|---|---|---|---|---|---|---|---|---|---|
| 17 | 125 | 250 | 120 | BD | MeOH (25) | MOC | Pd($\phi$CN)$_2$I$_2$[6] | CuI (25.0) | — |
| 18 | 125 | 1800 | 180 | BD | MeOH (25) | MOC | Pd(metal) | CuI (25.0) | LiI (10.0) |
| 19 | 100 | 1000 | 120 | BD | EtOH[7] (25) | EOC[8] | PdI$_2$ | CuI (25.0) | LiI (10.0) |
| 20 | 100 | 1000 | 120 | BD | PrOH[9] (25) | POC[10] | PdI$_2$ | CuI (25.0) | LiI (10.0) |
| 21 | 100 | 1000 | 180 | BD | BuOH[11] (25) | BOC[12] | PdI$_2$ | CuI (25.0) | LiI (10.0) |

Key
[1]BD - 1,3-butadiene
[2]MeOH - Methanol
[3]MOC - 1-methoxycyclohexene
[4]MOP - 2-methoxypropene
[5]IP - isoprene
[6]Pd($\phi$CN)$_2$I$_2$ - diodo-bis(benzo-nitrile) palladium (II)
[7]EtOH - ethyl alcohol
[8]ECO - 1-ethoxycyclohexene
[9]PrOH - propyl alcohol
[10]POC - 1-propoxycyclohexene
[11]BuOH - butyl alcohol
[12]BOC - 1-butoxycyclohexene

TABLE 3

| Ex. | Product | % Conversion | Mole % Ester Selectivity based on 1,3-butadiene |
|---|---|---|---|
| 5 | methyl penta-2,4-dienoate | 21 | 83 |
| 6 | methyl penta-2,4-dienoate | 15 | 79 |
| 7 | methyl penta-2,4-dienoate | 14 | 80 |
| 8 | methyl penta-2,4-dienoate | 16 | 81 |
| 9 | methyl penta-2,4-dienoate | 15 | 80 |
| 10 | methyl 3-methylpenta-2,4-dienoate | 13 | 77 |
| 11 | methyl 3-methylpenta-2,4-dienoate | 18 | 79 |
| 12 | methyl 3-methylpenta-2,4-dienoate | 17 | 80 |
| 13 | methyl penta-2,4-dienoate | 14 | 77 |
| 14 | methyl penta-2,4-dienoate | 12 | 80 |
| 15 | methyl penta-2,4 -dienoate | 15 | 81 |
| 16 | methyl penta-2,4-dienoate | 17 | 79 |
| 17 | methyl penta-2,4-dienoate | 17 | 43 |
| 18 | methyl penta-2,4-dienoate | 15 | 79 |
| 19 | ethyl penta-2,4-dienoate | 16 | 81 |
| 20 | propyl penta-2,4-dienoate | 14 | 80 |
| 21 | butyl penta-2,4-dienoate | 10 | 78 |

We claim:

1. A process for the preparation of a diene monoester having the formula

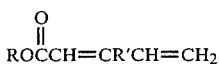

wherein R is an alkyl group of from 1 to 4 carbon atoms and R' is hydrogen, a halogen, or a methyl group which comprises reacting a diolefin having the formula

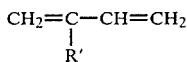

wherein R' is as above described, with a mixture of carbon monoxide and oxygen and at least a stoichiometric amount of an enol ether or 1-alkoxycycloalkene based on the diolefin employed, at a pressure of between about 15 psig and 5000 psig and at a temperature in the range of about 25° C. to 200° C. in the presence of an effective amount of a catalytic mixture of a platinum group metal compound selected from the group consisting of palladium, ruthenium, rhodium, and platinum, halides, cyanates, sulfates, nitrates, oxides, oxalates, acetates and trifluoroacetates or mixtures thereof, an organic mono- or poly-dentate ligand or coordination complex compound selected from the group consisting of alkyl, aryl and halogen-substituted phosphines, arsines, stibines and alkali metal salts, and a copper (I), copper (II), iron (II) or iron (III) oxidant salt compound and recovering the desired diene monoester.

2. A process according to claim 1 wherein the diolefin is selected from the group consisting of 1,3-butadiene and isoprene.

3. A process according to claim 2 wherein the diolefin is 1,3-butadiene.

4. A process according to claim 1 wherein the enol ether is 2-methoxypropene.

5. A process according to claim 1 wherein the 1-alkoxycycloalkene is selected from the group consisting of 1-methoxycyclohexene, 1-ethoxycyclohexene, 1-propoxycyclohexene or 1-butoxycyclohexene.

6. A process according to claim 5 wherein the 1-alkoxycycloalkene is 1-methoxycyclohexene.

7. A process according to claim 1 wherein the reaction is carried out in the presence of a catalytic amount of a monohydric saturated aliphatic, alcohol having from 1 to 4 carbon atoms which may contain other substituents which would not interfere with the reaction.

8. A process according to claim 7 wherein the alcohol is methyl alcohol, ethyl alcohol, propyl alcohol or butyl alcohol.

9. A process according to claim 8 wherein the alcohol is methyl alcohol.

10. A process according to claim 1 wherein the pressure is between about 100 psig and 2000 psig.

11. A process according to claim 1 wherein the temperature is in the range of from about 80° C. to 150° C.

12. A process according to claim 1 wherein the platinum group metal compound is selected from palladium (II) bromide, palladium (II) iodide, rhodium (III) iodide, platinum (II) iodide, sodium iodopalladate, potassium iodopalladate and diiodo-bis(benzo-nitrile)palladium (II).

13. A process according to claim 12 wherein the platinum group metal compound is palladium (II) iodide.

14. A process according to claim 12 wherein the platinum group metal compound is palladium (II) bromide.

15. A process according to claim 1 wherein the oxidant salt compound is selected from the group consisting of copper (I), copper (II), iron (II) and iron (III) halides, sulfates, trifluoroacetates, oxalates, naphthenates, nitrates and acetates.

16. A process according to claim 15 wherein the oxidant salt is selected from the group consisting of copper (I) iodide, copper (II) bromide, and iron (II) iodide.

17. A process according to claim 16 wherein the oxidant salt compound is copper (I) iodide.

18. A process according to claim 16 wherein the oxidant salt compound is copper (II) bromide.

19. A process according to claim 16 wherein the oxidant salt compound is iron (II) iodide.

20. A process according to claim 1 wherein the ligand or coordination complex is lithium iodide.

21. A process according to claim 1 wherein the ligand or coordination complex is lithium bromide.

22. A process for the preparation of methyl penta-2,4-dienoate which comprises reacting 1,3-butadiene with a mixture of carbon monoxide and oxygen, at least a stoichiometric quantity of 1-methoxycyclohexene based on the butadiene employed at a pressure of between about 100 psig and 2000 psig and at a temperature in the range of from about 80° C. to 150° C. in the presence of an effective amount of a palladium metal salt compound and a copper (I) oxidant salt compound.

23. A process according to claim 22 wherein the palladium metal salt compound is palladium (II) iodide, and the copper (I) oxidant salt compound is copper (I) iodide.

24. A process according to claim 23 wherein the reaction is carried out in the presence of a catalytic amount of lithium iodide.

* * * * *